United States Patent
Slone et al.

(10) Patent No.: US 11,378,569 B2
(45) Date of Patent: Jul. 5, 2022

(54) SMOKE TAINT SENSING DEVICE

(71) Applicants: Simple Labs, Inc., Coto de Caza, CA (US); KWJ ENGINEERING, Inc., Newark, CA (US)

(72) Inventors: Michael Slone, Coto de Caza, CA (US); Melvin Findlay, Richardton, ND (US); Joseph R. Stetter, Livermore, CA (US)

(73) Assignees: Simple Labs, Inc., Coto de Caza, CA (US); KWJ ENGINEERING, Inc., Newark, CA (US)

( * ) Notice: Subject to any disclaimer, the term of this patent is extended or adjusted under 35 U.S.C. 154(b) by 0 days.

(21) Appl. No.: 17/446,329

(22) Filed: Aug. 30, 2021

(65) Prior Publication Data

US 2022/0065843 A1    Mar. 3, 2022

Related U.S. Application Data

(60) Provisional application No. 63/072,537, filed on Aug. 31, 2020.

(51) Int. Cl.
  *G01N 33/14* (2006.01)
  *B65D 39/04* (2006.01)
  (Continued)

(52) U.S. Cl.
  CPC ......... *G01N 33/4972* (2013.01); *B65D 39/04* (2013.01); *C12H 1/16* (2013.01);
  (Continued)

(58) Field of Classification Search
  CPC .... G01N 33/146; G01N 33/4972; C12H 1/16; B65D 39/04; Y10T 436/20;
  (Continued)

(56) References Cited

U.S. PATENT DOCUMENTS 6,541,260 B1 *  4/2003  Pariseau .............. G01N 33/146
                                                            436/24
7,992,426 B2    8/2011  Fleischer et al.
                        (Continued)

FOREIGN PATENT DOCUMENTS

CN      203033109 U    7/2013
WO      1996004550 A1  2/1996
                (Continued)

OTHER PUBLICATIONS

Singh et al. Australian Journal of Grape & Wine Research, vol. 17, pp. S13-S21, 2011.*

(Continued)

*Primary Examiner* — Maureen Wallenhorst
(74) *Attorney, Agent, or Firm* — MLO, a professional corp.

(57) ABSTRACT

A plug for a container for storing liquid includes a housing and an input end at an end of the housing, the input end having a liquid-impermeable membrane that allows gas flow to pass through. A first sensor is in a first sensor chamber inside the housing, the first sensor being configured to detect a smoke taint compound. A first filter is between the input end and the first sensor, where the first filter selectively allows phenols to pass through. A second sensor is in a second sensor chamber inside the housing, the second sensor being configured to detect a second substance different from the smoke taint compound. A second filter is between the input end and the second sensor, wherein the second filter selectively allows the second substance to pass through.

20 Claims, 11 Drawing Sheets

(51) Int. Cl.
*G01N 33/497* (2006.01)
*C12H 1/16* (2006.01)

(52) U.S. Cl.
CPC .. *G01N 33/146* (2013.01); *Y10T 436/203332* (2015.01); *Y10T 436/255* (2015.01); *Y10T 436/25375* (2015.01); *Y10T 436/25875* (2015.01)

(58) Field of Classification Search
CPC ... Y10T 436/203332; Y10T 436/25375; Y10T 436/255; Y10T 436/25875
USPC ......... 436/24, 127, 131, 149, 151, 177, 178, 436/181; 422/82.01, 82.04, 83, 98, 534
See application file for complete search history.

(56) References Cited

U.S. PATENT DOCUMENTS

| | | |
|---|---|---|
| 8,365,758 B2 | 2/2013 | Maiocco |
| 9,221,667 B2 | 12/2015 | Hershberger et al. |
| 9,535,044 B2 | 1/2017 | Kim et al. |
| 9,784,708 B2 | 10/2017 | Stetter et al. |
| 10,267,667 B2 | 4/2019 | Gurumohan et al. |
| 10,386,325 B2 | 8/2019 | Xiao et al. |
| 2004/0076946 A1 | 4/2004 | Trauner et al. |
| 2005/0249851 A1* | 11/2005 | Wollan ............ C12H 1/16 426/422 |
| 2013/0317764 A1 | 11/2013 | Kumar et al. |
| 2015/0000371 A1 | 1/2015 | Greene et al. |
| 2015/0198474 A1 | 7/2015 | Howard |
| 2015/0247814 A1* | 9/2015 | Hofmann ............ G01R 33/30 324/307 |
| 2015/0293067 A1 | 10/2015 | Greene et al. |
| 2018/0136020 A1 | 5/2018 | Sweet |
| 2019/0154571 A1 | 5/2019 | Kuczynski et al. |
| 2020/0158708 A1 | 5/2020 | Nogueira et al. |
| 2020/0172842 A1* | 6/2020 | Wu, Jr. ............ C12H 1/0424 |

FOREIGN PATENT DOCUMENTS

| | | |
|---|---|---|
| WO | 2002033404 A2 | 4/2002 |
| WO | 2018116186 A1 | 6/2018 |
| WO | 2018141836 A1 | 8/2018 |

OTHER PUBLICATIONS

Fudge et al. Food Chemistry, vol. 139, pp. 115-119, Feb. 9, 2013.*
International Search Report and Written Opinion dated Dec. 3, 2021 for PCT Patent Application No. PCT/IB2021/057916.
Krstic, M. P. et al., "Review of smoke taint in wine: smoke-derived volatile phenols and their glycosidic metabolites in grapes and vines as biomarkers for smoke exposure and their role in the sensory perception of smoke taint", Australian Journal of Grape and Wine Research, 2015, vol. 21, pp. 537-553. abstract; p. 542.
Dennison et al., "Gas-Phase Microbiosensor for Monitoring Phenol Vapor at ppb Levels," Anal. Chem, Nov. 1995, vol. 67, Issue 21, p. 3922 (First page accessed only.).
Theron, "The use of cordless smart barrel bungs," WineLand Media, Jul. 1, 2017, 3 pages.
Williams, Understanding Smoke Taint, Wine Spectator, Nov. 3, 2017, 8 pages, https://www.winespectator.com/articles/understanding-smoke-taint-in-wine.

* cited by examiner

SMOKE TAINT SENSING DEVICE

RELATED APPLICATIONS

This application claims priority to U.S. Provisional Application No. 63/072,537, filed on Aug. 31, 2020, and entitled "Smoke Taint Sensing Device," which is hereby incorporated by reference in full.

BACKGROUND

As wildfires occur more frequently throughout the world, such as in California and Australia, one impact of these fires is on wine production. When grapes are exposed to smoke from nearby fires, chemicals from the smoke can bond to the grape skins. This condition is called smoke taint. If not detected early in the wine fermentation process, smoke taint can make the resulting wine taste bitter, burnt and ashy, rendering the wines unsalable. Damage due to smoke taint has resulted in losses of tens of millions of dollars per year to the wine industry.

Compounds that have been established as indicators of smoke taint are guaiacol, 4-methylguaiacol, and related phenols. Known methods for identifying smoke taint are typically based on wet chemistry. For example, juice or wine samples are collected, sent to a laboratory for analytical testing, and the results are returned in several days or even weeks. Analytical testing performed by the labs can include liquid chromatography and mass spectrometry.

In more general practices of determining wine quality, devices that have been used include electrochemical sensors and optical chemical sensors that analyze a liquid. These sensors have been installed in the walls or corks of bottles or barrels, such as electrochemical sensors performing wet chemistry by directly contacting wine. For example, "smart barrel bungs" are known in the industry and typically have probes that contact the alcohol liquid to measure quantities such as pH, carbon dioxide, sulfite and oxygen. Environmental sensors such as for temperature and humidity can also be included in these bungs.

SUMMARY

In some embodiments, a plug for a container for storing liquid includes a housing and an input end at one end of the housing, the input end having a plurality of chambers. A first sensor is in a first sensor chamber inside the housing, the first sensor being configured to detect guaiacol. A first filter is near the input end of the plug, where the first filter selectively allows phenols including guaiacol to enter a first input chamber of the plurality of chambers. A first flow pathway is between the first sensor chamber and the first input chamber. A second sensor is in a second sensor chamber inside the housing, the second sensor being configured to detect a second substance different from the phenols. A second filter is near the input end of the plug, where the second filter selectively allows the second substance to enter a second input chamber of the plurality of chambers. A second flow pathway is between the second sensor chamber and the second input chamber.

In some embodiments, a plug for a container for storing liquid includes a housing and an input end at an end of the housing, the input end having a liquid-impermeable membrane that allows gas flow to pass through. A first sensor is in a first sensor chamber inside the housing, the first sensor being configured to detect a smoke taint compound. A first filter is between the input end and the first sensor, where the first filter selectively allows phenols to pass through. A second sensor is in a second sensor chamber inside the housing, the second sensor being configured to detect a second substance different from the smoke taint compound. A second filter is between the input end and the second sensor, wherein the second filter selectively allows the second substance to pass through.

DETAILED DESCRIPTION

Figure 1A:
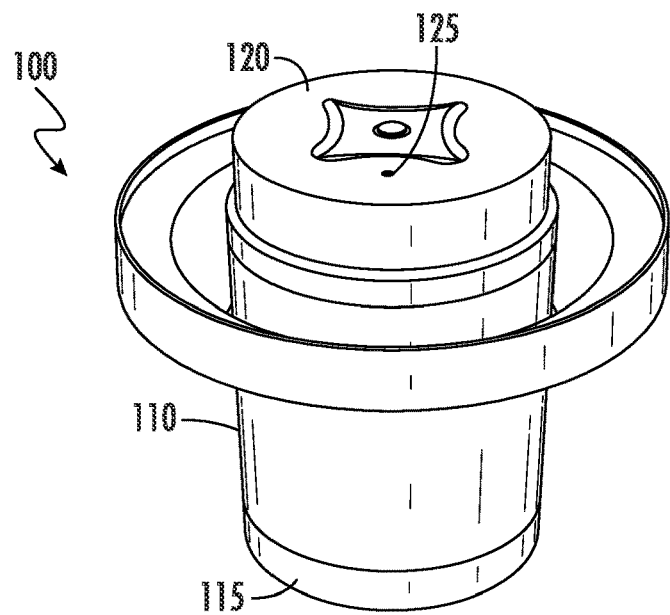
FIGS. 1A-1B are perspective views of a sensor plug for a container for storing liquid, in accordance with some embodiments.

In the present disclosure, sensors for detecting smoke taint are incorporated into a plug (i.e., bung) for a container that holds liquids, such as a container used to age alcoholic beverages. The container may be, for example, a wine barrel, stainless steel tank, fermentation tank, micro-fermentation bucket, cask, or steel or wooden vat. The plug is inserted into a hole in the container, thereby sealing the container while taking measurements of the contents within the container during storage and/or aging of the contents. The sensors analyze ions and particles carried by gases that are released by the aging wine, spirits or other liquid into the container, thus eliminating the need to contact the liquid for sampling and also reducing the time for results to be obtained compared to wet chemistry. The sensors include gas sensors, such as electrochemical gas sensors. Embodiments can also include other types of sensors such as liquid, ultrasonic and/or optical sensors that work in conjunction with the gas sensors. The plug includes selective filters that reduce or eliminate the amount of substances other than the target substances from entering the plug, thereby increasing the accuracy of the detection since extraneous substances are filtered out.

In some embodiments, the plug has input chambers through which substances (e.g., ions, particles, gases, compounds, molecules) are carried into the plug by a gas or vapor. The input chambers have specific filters to limit non-target substances from entering the plug. The plug is constructed to channel an individual gas from an input chamber to a corresponding sensor type, thereby providing a high level of detection accuracy by reducing cross-contamination from other gases. Devices of the present disclosure enable ongoing and accurate monitoring of wine quality (or quality of other liquid being stored) with results being available in real-time, thus providing advantages over conventional smoke taint testing where physical samples must be taken and days elapse before results are known. Having plugs installed on barrels (or other containers) also enables identification of individual barrels within a batch that might be contaminated with smoke taint or other contaminants (e.g., bacteria).

Although embodiments shall be described primarily in terms of being used for wine, embodiments can be applied to spirits such as whiskey, rum, tequila, cognac and the like. In addition, embodiments can be applied to other types of liquids housed in containers such as water that might encounter smoke taint during storage. The plugs can also be used on containers taken into the field, in addition to being used on storage containers. For example, grapes in different areas of a vineyard can be crushed and micro-fermented in containers in the field, enabling grapes to be sampled for smoke taint before harvesting. Plug devices can be attached to the containers to achieve quick readings on possible smoke exposure, to help the winemaker determine next steps. Another use case for the plug devices is for empty barrel storage. For instance, decreasing sulfur dioxide ($SO_2$) levels and/or an increase in internal humidity levels can indicate an environment with a higher risk of bacteria or other unwanted microorganism growth.

In the present disclosure, substances being identified by the plug can be particles, ions, compounds, molecules and/or other forms of analytes. The substances enter the plug generally by a gas or vapor that carries the substances. References to a gas or gas flow in this disclosure shall also apply to vapor or vapor flow. In some embodiments, additional sensors can also be used to sample substances directly from the liquid in the container, where readings from the liquid measurements can be utilized with the readings from sensors inside the plug. In this disclosure, references to a particular type of storage container such as a barrel for wine aging can also apply to other types of containers such as casks, tanks, and the like.

Figure 1B:
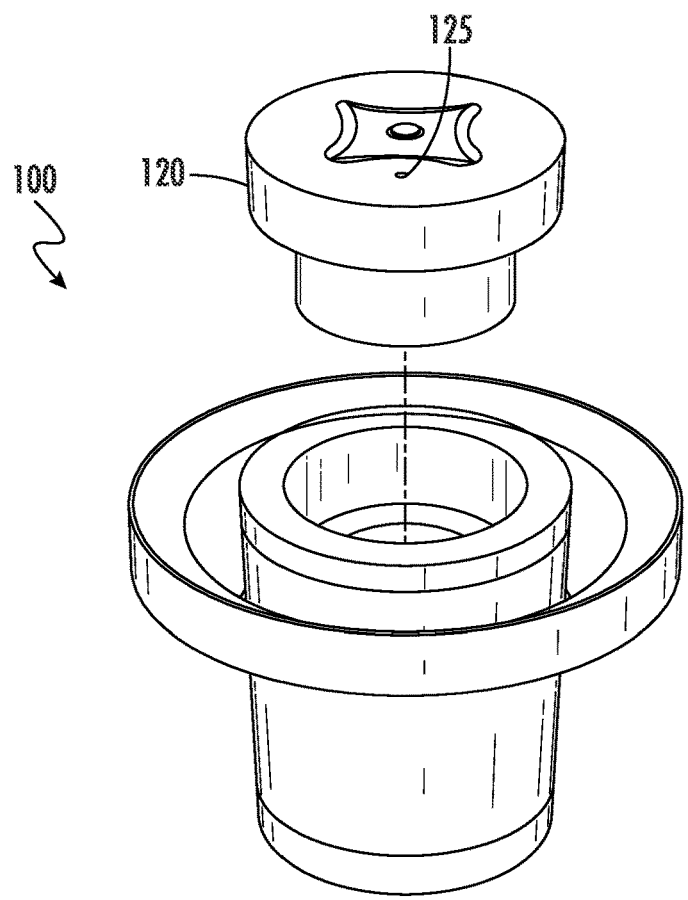

FIG. 1A shows a perspective view of an example plug 100 in accordance with some embodiments, and FIG. 1B is a bottom perspective view of the plug 100. The plug 100 has a housing 110 with an input end 115 where gases and vapors from the liquid storage container will enter the plug. A battery 120 at the opposite end is detachable as shown in FIG. 1B so that it can be periodically replaced or recharged. In some embodiments, the plug 100 can include an indicator light 125 to notify a user when the battery 120 needs to be replaced—such as the light turning from green to red (e.g., FIG. 1A vs. 1B).

Figure 2:
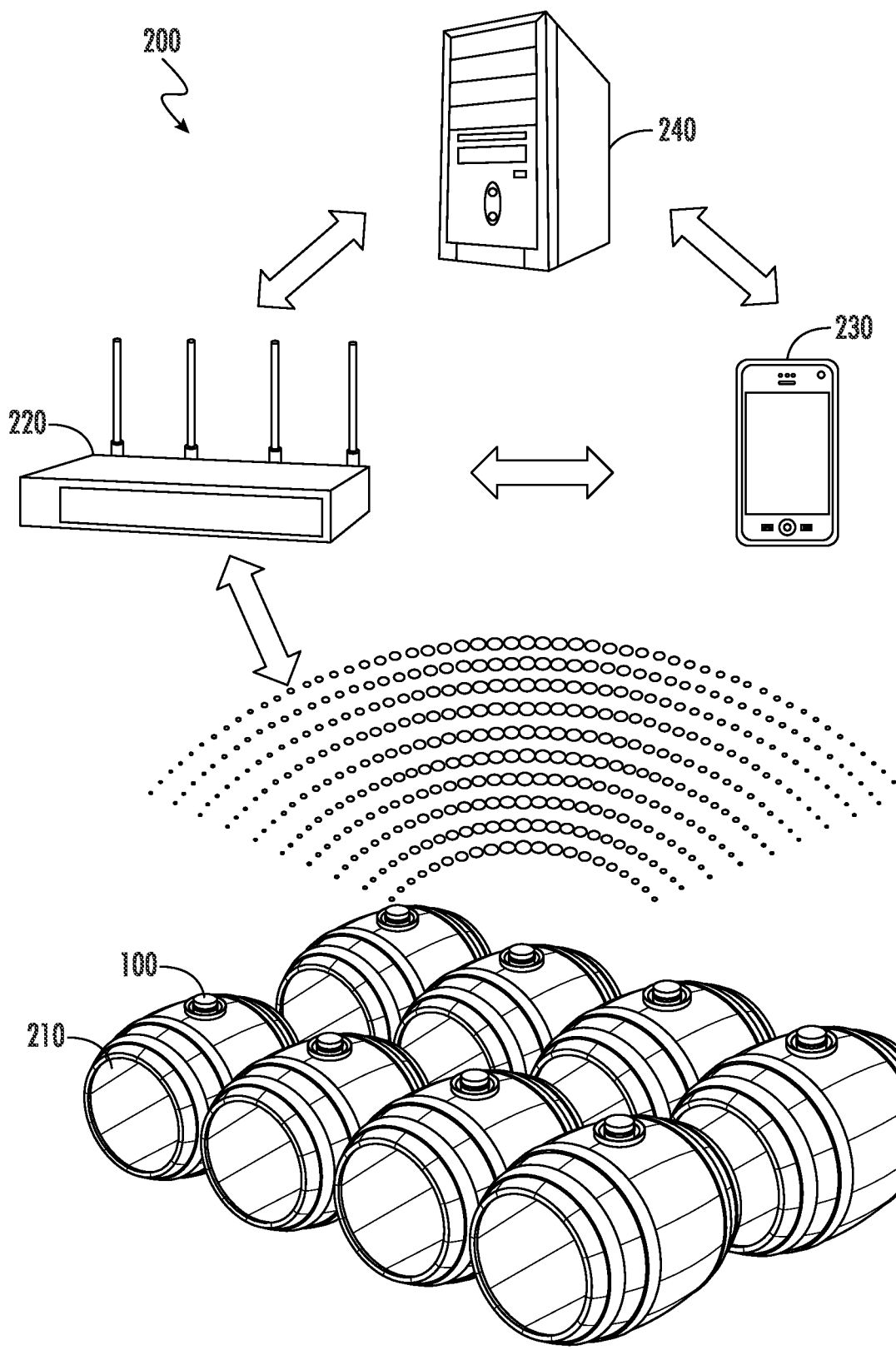
FIG. 2 is a schematic of a system that uses the sensor plugs of FIGS. 1A-1B, in accordance with some embodiments.

FIG. 2 shows an example system 200 utilizing plugs of the present disclosure, where the plugs 100 are installed on barrels 210 and networked together such as through a Wifi hub 220. The plugs 100 enable many barrels to be monitored on a periodic or ongoing basis, providing a greatly improved sampling compared to having to take physical samples of isolated barrels at individual points in time. Having plugs on individual barrels enables identification of specific barrels that have problems, rather than having to discard the entire batch. In some embodiments, multiple devices can be placed in different locations across the storage facility and at different heights in the stacks of barrels. Comparisons can then be performed and adjustments to the climate controls made as needed to optimize aging as well as energy efficiency.

The plugs can communicate with a mobile device 230 (e.g., smart phone, tablet, smart watch) using wireless technology such as BLUETOOTH®. The plugs send information such as updates or warnings to a user's device regarding measured values, such as to provide periodic reports or to inform the user when the measured values are out of tolerance ranges. The system 200 (e.g., using a central processor 240) can receive data measurements from the plugs, analyze the current levels and the recorded data, and make recommendations on actions to take as next steps. The tolerance ranges may be default settings provided by the system (e.g., based on recommended industry standards) or set by the user. The tolerance ranges can be for values of the measurements or for changes in the values, such as rising or falling trends. Measurements taken by the plug can include presence of smoke taint compounds as well as other aspects that affect quality of the in the container (e.g., wine, other alcohol or spirit being aged, or non-alcoholic liquids). Measurement results can be presented on a web application for a user to view current and historical results. Embodiments can include augmented reality such as to visually display the location of a particular barrel that has conditions that exceed a tolerance range.

Smoke taint indicators that can be detected by the plugs of the present disclosure include various phenols, such as volatile phenols. Examples of smoke taint compounds include guaiacol, 4-methylguaiacol, cresols (m-cresol, o-cresol, p-cresol), syringol, and trans-resveratrol. Examples of other substances that can be detected by the plugs for determining the quality of the wine or other liquid include acetic acid, $SO_2$ and hydrogen. Acetic acid is produced by the bacterium acetobacter, which is used in the production of vinegar and is also associated with wine spoilage. Acetic acid can result from too much oxidation, in which wine can become oxidized to the point that acetaldehyde converts to acetic acid. Sulfur dioxide can help prevent oxidation and reduce bacterial growth and can also impact the aromas and flavors of wine. Hydrogen can be used to indicate pH level, where low pH wines will taste tart and crisp while higher pH wines are more susceptible to bacterial growth.

Figure 3A:
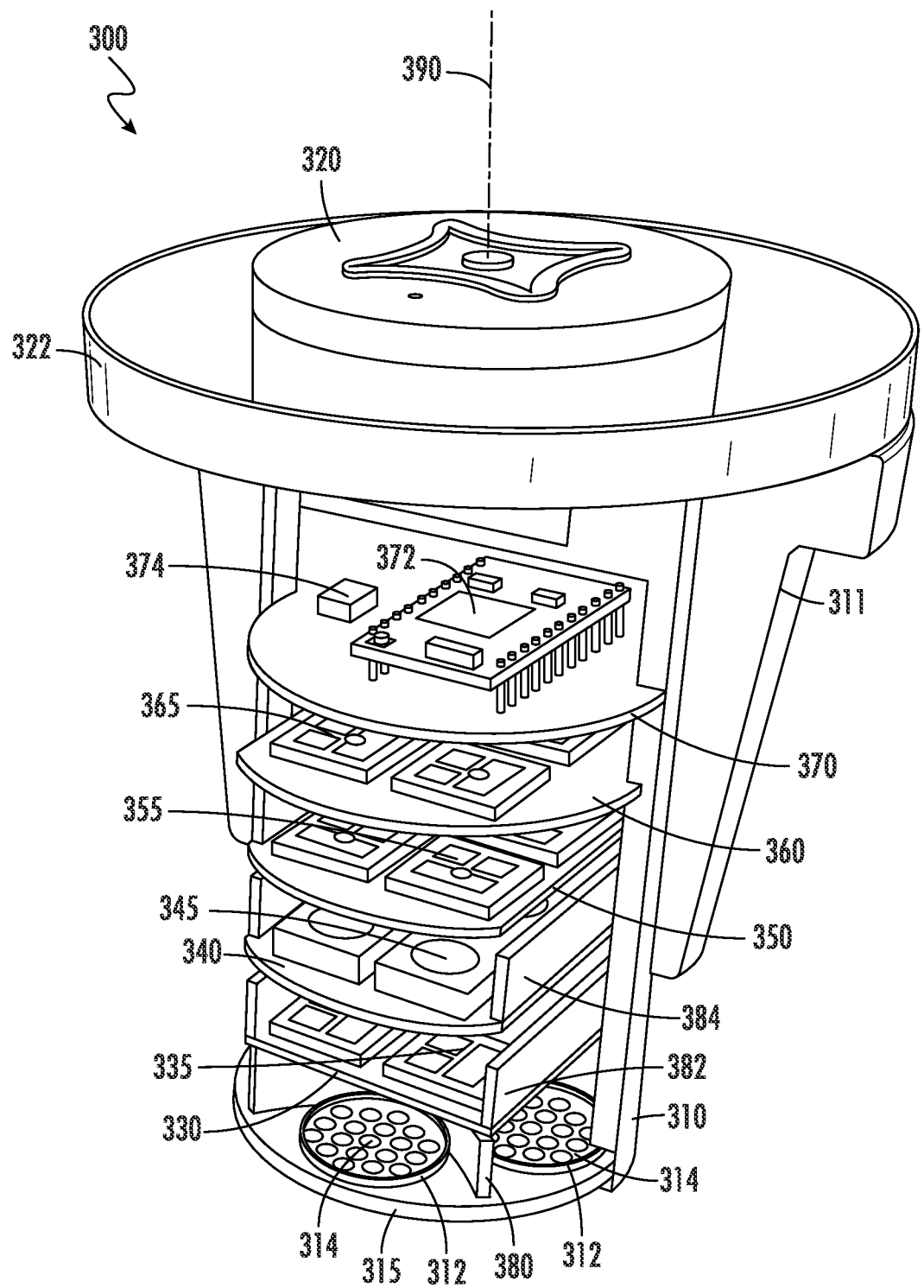
FIG. 3A is a partial cut-away view of a sensor plug device, in accordance with some embodiments.

FIG. 3A is a cut-away view of a plug 300 for inserting into a hole in a container's wall, in accordance with some embodiments. The container may be for aging spirits, for instance. Similar to plug 100 of FIGS. 1A-1B, plug 300 has a housing 310 with an input end 315. Housing 310 can be made of a single material or can be made of more than one layer. In the illustrated embodiment, the plug 300 has two layers—a primary housing 310 that is encased by an outer sleeve 311. Housing 310 serves as the structural framework for the internal components of the plug. Materials for housing 310 can include, for example, stainless steel, food-grade aluminum, a polymer (e.g., polyethylene) or glass. The outer sleeve 311 can be a deformable, elastomeric material such as silicone to ensure a tight fit with an opening in the storage container (e.g., barrel) into which the plug is inserted. Materials for housing 310 and sleeve 311 are food-grade, non-disruptive to the aging process, and non-corrosive to withstand the chemical and environmental conditions of the fermentation or aging process in the container.

At the upper end of plug 300, which will be external to the storage container when the plug is installed, is a device battery 320. The battery 320 may be coupled to the plug 300 with mechanisms for easy replacement or to allow easy attachment and detachment for recharging. For example, the battery 320 may be coupled to the plug 300 magnetically or with a threaded engagement, snap fit, or other mechanical means. A ring 322 is also near the top end of the plug to limit how far the plug is inserted into the barrel. The ring may be a disk that is sized to be larger than the opening of the barrel where the plug will be installed. The ring is a clear material in this embodiment but may be other colors as desired aesthetically.

Within the plug 300 are several printed circuit boards (PCBs) stacked over one another along a longitudinal axis 390 of the housing. The longitudinal axis 390 runs along a length of the plug 300 from the input end 315 to the ring 322. Longitudinal axis 390 may be a central axis, such as at the center of the cylindrical housing, or may be offset from center. The uppermost PCB 370 in this embodiment holds a control board 372 that includes electronic components for running the sensors and for the overall operation of the plug device. The control board 372 may include, for example, computing processors for storing and calculating (e.g., averaging or aggregating) measurements, components for Wifi and BLUETOOTH, and a power supply (e.g., a battery) along with power connections between the battery and sensors. Other processing boards may also be included on control board 372 for other communication protocols such as long-range networks (LoRa) and/or personal wireless mesh networks (e.g., Zigbee) as needed for the specifics of the storage container location. For example, the storage containers may be located in underground caves, in open above-ground warehouses, or combinations of these environments, each of which may require different networking links due to the physical constraints of the location. In addition, owners of the storage locations may configure their facilities differently from each other, such as with or without internal mesh networking. Various networking set-ups can be accommodated by the plug 300 by including processing boards appropriate for the customer's specifications.

Also included in control board 372, in this embodiment, is a temperature and humidity sensor 374 for measuring internal temperature and humidity within the storage container. Temperature and humidity sensor 374 may be configured to measure, for example, temperature in a range of −40° C. to 80° C. with ±0.5° C. accuracy; and humidity of 0% to 100% with 2%-5% accuracy. Plug 300 may also include an external temperature and humidity sensor (not shown) to measure conditions external to the barrel. For example, external temperature and/or humidity sensors may be located on an external surface of the ring 322, where the external surface will remain outside the barrel when the plug 300 is installed.

Figure 3B:
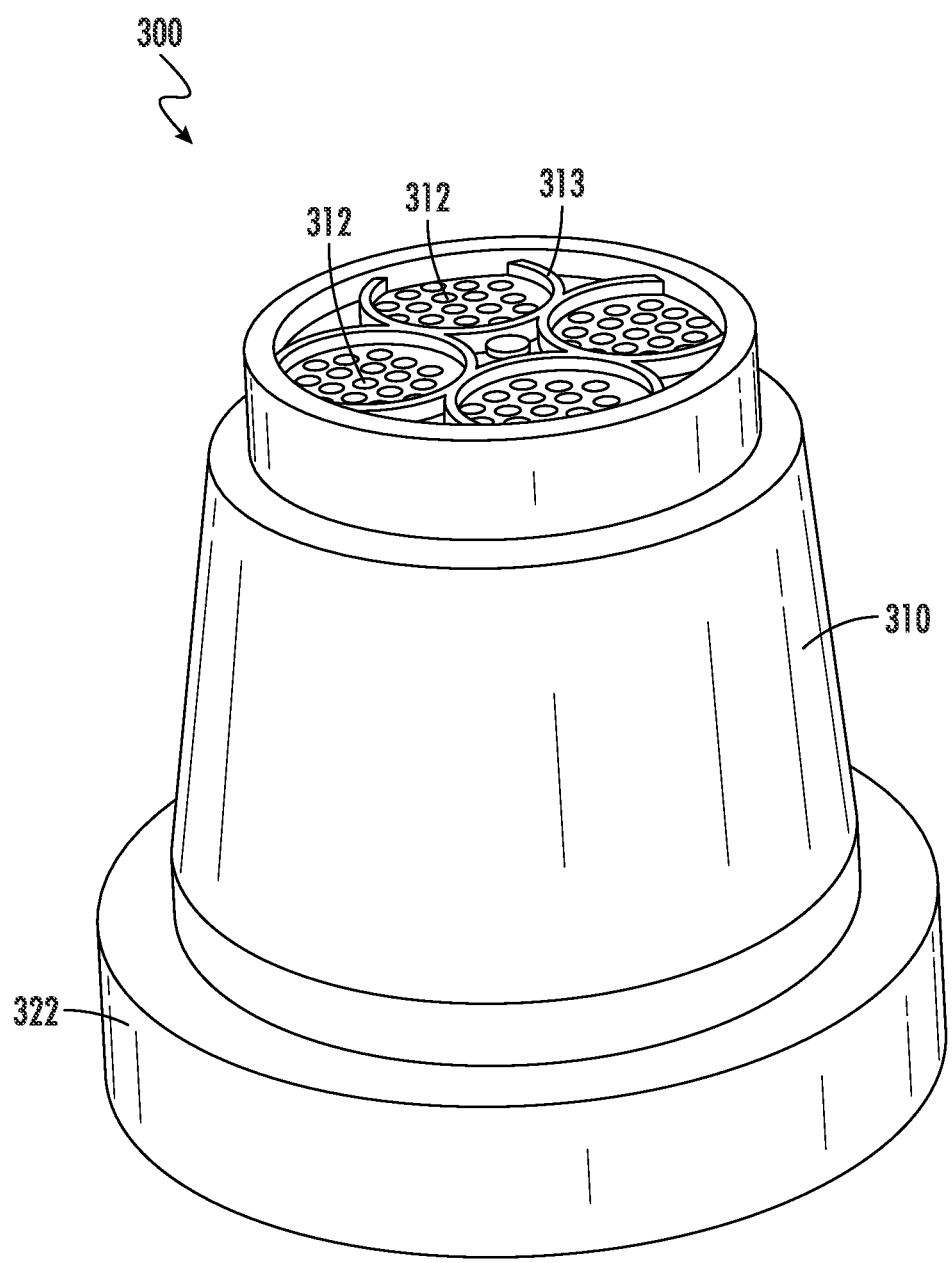
FIG. 3B is a bottom perspective view of the sensor plug device of FIG. 3B, in accordance with some embodiments.

To detect smoke taint, gases and vapors from the storage container enter the bottom of the plug 300 at input end 315, through a plate with mesh openings 312 covered by filters 314. The mesh openings 312 are also shown in the bottom perspective view of FIG. 3B. The mesh openings 312 allow gases to enter the plug, while also protecting the filters 314 from damage, such as from getting punctured during handling or usage. The gases and vapors carry ions, molecules and/or particles of substances of interest for monitoring the stored liquid. The mesh openings are configured in this embodiment as a circular array of circular openings but may be configured with other geometries such as rectangular or triangular lattices/grids covering a circular, rectangular, or triangular area. All the mesh opening arrays in FIG. 3B are the same in this embodiment but may be different from each other in other embodiments. For example, one mesh opening 312 may have fewer holes than another mesh opening or may have different sizes or different arrangement of holes (e.g., holes arranged in lines, concentric rings, or staggered or in-line arrays).

Each mesh opening 312 may be covered with a different filter 314 (FIG. 3A), where the filters are configured to allow only the desired substances to enter the plug. That is, each filter 314 selectively allows a specific substance or substances to pass through, while preventing or greatly reducing the amount of undesired substances from entering the plug. The filters may, for example, absorb or entrap the undesired substances, thus preventing or greatly reducing the amount of those non-targeted substances from permeating the filter. The filters can be, for example, particle-specific absorbing filters which can be made of a glass fiber matrix that is embedded with absorbents, additives or catalysts that absorb or react with unwanted substances. In the embodiment of FIG. 3A, the filters 314 are separated from each other by divider walls 380 in an interior of the input end 315, to form an input chamber for each filter.

In some embodiments, filters 314 provide filtering of specific substances for detection, and are also liquid-proof to allow gases and air to enter the plug while keeping liquid out. In other embodiments, filters 314 may include a separate membrane to provide the liquid-impermeable capability. The membranes may be, for example, hydrophobic membranes that serve as liquid-repellent vent filters. In one example, the membranes can be cross flow microfiltration membranes that are sintered to allow bidirectional gas flow (with molecules, compounds particles and ions carried by the gas) and still remain watertight. Since wine barrels are ideally completely filled, the input end 315 of the plug 300 is submerged under the liquid level within the storage container. The watertight filters or membranes prevent liquid from entering the plug, while still allowing entry of gases that carry substances to be detected. The filters 314 (and/or membranes) may be detachably coupled to the plug to enable periodic replacement or cleaning. For example, the filters and/or membranes may be located inside the plug, in the chambers formed by the divider walls 380 of FIG. 3A. In some embodiments, the filters and/or membranes may be located in a compartment formed by raised walls 313 (FIG. 3B) on an exterior surface of the mesh openings 312. The compartments comprise a wall 313 around each mesh opening 312, where the wall forms a recess into which a membrane and/or filter can be placed. The compartments may include a retaining piece for coupling the filter or membrane to the plug, such as by a threaded mechanism, snap fit, sliding component or other methods.

Returning to FIG. 3A, sensor PCBs 330, 340, 350 and 360 contain sensors to detect various substances or environmental factors. Each of the sensor PCBs may contain a single sensor or may contain multiple sensors (which shall be referred to as a "sensor bank"), where in some embodiments the multiple sensors can be used for redundancy or for averaging measurements. Using data from multiple sensors for the same substance can provide more reliable measurements than one measurement from a single sensor. When averaging data sensed by a plurality of sensors, the plug can include a processor such as a calculation processing board (e.g., control board 372) on one of the printed circuit boards in the plug. In some embodiments, the multiple sensors can be different types of sensors that can be used to triangulate (i.e., derive, calculate) the presence of a substance. The substances detected by the sensors can be particles, ions, compounds, molecules or other substances carried by gases or vapors in the storage container.

In an example embodiment for monitoring wine, sensor PCB 330 has sensors 335 to detect acetic acid. The acetic acid sensor 335 can be configured to detect acetic acid particles at, for example, 0 to 1000 parts per million (ppm), with a lower limit of 0.3 ppm and resolution of 0.15 ppm. A second sensor PCB 340 has sensors 345 to detect one or more smoke taint compounds, such as digital volatile organic compounds (VOC) in a concentration of 0 to 1000 ppm, with a lower detection limit of 10 ppm, and resolution 2 ppm. The smoke taint compound may be detected by identifying phenols, including guaiacol and 4-methylguaiacol. As shall be described later in this disclosure, a plurality of sensors 345 can uniquely be configured to detect elements of phenols, such as carbon-oxygen bonds or carbon-carbon aromatic bonds, to deduce the presence of smoke taint compounds.

A third sensor PCB 350 has sensors 355 to detect hydrogen ($H_2$) or hydroperoxyl ($O_2$), where hydrogen measurements from sensors 355 are used to calculate or track trends in the pH level. The sensors 355 may be configured to detect hydrogen at, for example, a concentration of 0 to 1000 ppm, with a lower detection limit of 10 ppm and resolution of 2 ppm. A final sensor PCB 360 in plug 300 has sensors 365 for detecting sulfur dioxide ($SO_2$), such as in a range of 0 to 20 ppm with a lower detection limit of 0.3 ppm and resolution 0.15 ppm. Sensors for detecting other compounds released by the aging wine or for detecting other factors relevant to wine quality (e.g., air pressure) may also be included in the plug device.

The sensor PCBs 330, 340, 350 and 360 are spaced apart vertically from each other and from PCB 370 along longitudinal axis 390 such that the sensors on each sensor PCB can be exposed to gas and particles entering the plug. Each sensor PCB is oriented horizontally (i.e., transverse to the longitudinal axis 390) within the plug 300 and forms a sensor chamber bounded vertically by the circuit board itself and the PCB above it. Each sensor chamber is bounded laterally by the housing 310 and/or walls on one or more edges of the PCB. For example, sensor PCB 330 has a wall 382 that extends from PCB 330 to PCB 340, and sensor PCB 340 has a wall 384 that extends from PCB 340 to PCB 350. Note that the height of walls 382 and 384 are shown as only partially extending between PCBs in this illustration for clarity, but in actuality will extend fully between PCBs to seal the walls of the chambers.

Figure 4A:
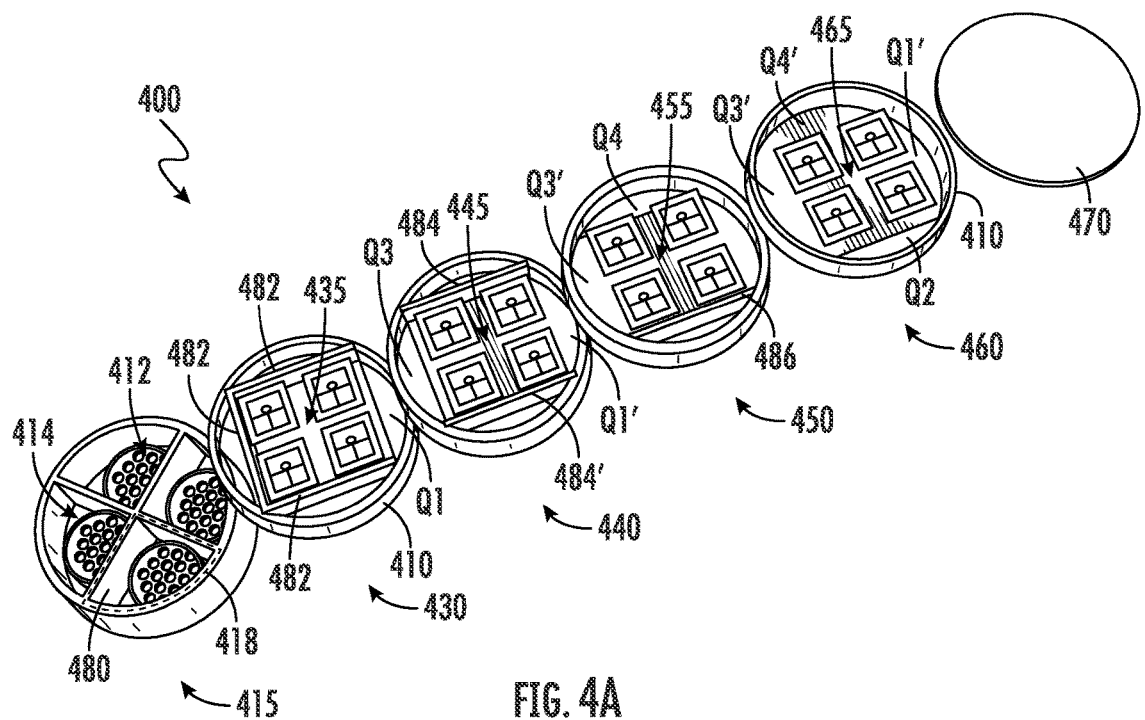
FIG. 4A shows sectional layers of a sensor plug device, in accordance with some embodiments.
Figure 4B:
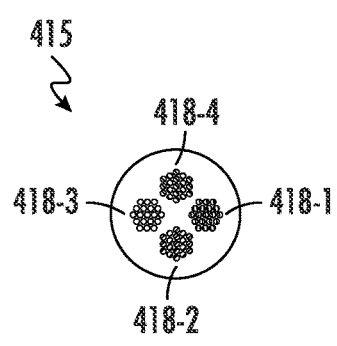
FIG. 4B is a schematic of input chambers of the device of FIG. 4A, in accordance with some embodiments.
Figure 4C:
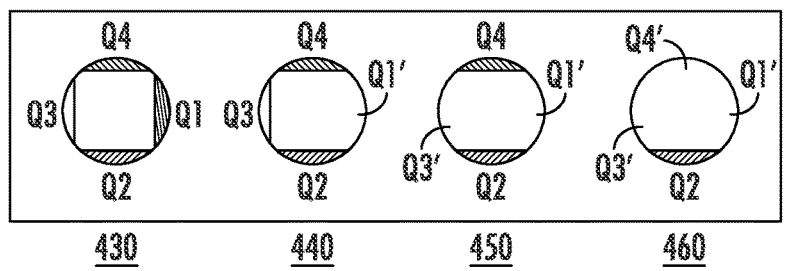
FIG. 4C is a schematic of flow pathway channels of the device of FIG. 4A, in accordance with some embodiments.

FIGS. 4A-4C provide further details of the sensor chambers of a plug 400, in accordance with some embodiments. FIG. 4A shows sectional slices of various layers of the plug 400, FIG. 4B is a schematic of input chambers at the input end 415, and FIG. 4C schematically shows flow pathway channels formed by each of the layers. Gases from the storage container (e.g., barrel) enter the input end 415 of the plug which is divided into a plurality of chambers 418. In the illustrated embodiment there are four input chambers 418 shaped as equal-sized quadrants of the circular cross-section of the housing and arranged radially around a longitudinal axis (axis 390 of FIG. 3) of the housing. The input chambers are created by divider walls 480 that are placed on the plate at the input end of the device. Other arrangements of the chambers 418 may be possible, to accommodate the arrangement of sensor chambers in the plug. For example, more or less than four chambers may be used, or the chambers may be arranged with geometries other than radial segments. Each chamber 418 is configured with a filter 414 covering a mesh opening 412, thus allowing only a particular substance to pass through (i.e., substantially removing other substances). The filters are substance-specific by being designed to absorb or entrap one or more target substances. One filter of the plug device allows only phenols (including guaiacol) to enter in order to detect a smoke taint compound, while the other filters allow one or more substances different from phenols to enter.

Each input chamber 418 at the input end 415 communicates with a sensor chamber 430, 440, 450 or 460. Each of the sensor chambers contains a sensor bank that is configured to detect a substance corresponding to a chamber 418 that is in fluid communication with (i.e., connected by a gas flow pathway) the sensor bank. For example, continuing the embodiment of FIG. 3, sensors in sensor chamber 430 may be configured to detect acetic acid, sensor chamber 440 may be for phenol/guaiacol, sensor chamber 450 may be for hydrogen, and sensor chamber 460 may be for $SO_2$. Other combinations of target substances may be used in other embodiments. In the embodiment of FIG. 4A, four sensors are in each sensor bank (i.e., mounted on one PCB), although other numbers of sensors such as one to three, or more than four, are possible. The sensors in each sensor bank may be electrochemical sensors, such as printed gas sensors (e.g., fabricated by screen printing). Electrochemical sensors beneficially enable rapid measurements to be achieved (e.g., within seconds or minutes), compared to conventional wet chemistry results for smoke taint markers which can take days or weeks. Printed gas sensors advantageously enable sensors having a small enough size to be compatible for a plug to fit into conventional bunghole sizes (e.g., 2-inch diameter). Using small-sized sensors also provides a benefit of using low amounts of electrical current to power them. In some embodiments, the electrochemical sensors can have a power-saving mode, being dormant when not in use to reduce battery usage.

The sensors are mounted on the PCBs in a square-shaped arrangement in FIG. 4A, leaving unoccupied areas between the edges of the PCBs and the housing. That is, one or more of the unoccupied circular segments at the edges of the PCBs are cut off of the circular PCBs. These unoccupied areas serve as open spaces through which the gases can flow from the input end to the appropriate sensor PCB, as shown by the schematic of the gas flow paths in FIGS. 4B and 4C. As shall be described below, these open spaces are uniquely used as channels for gases to flow from their respective receiving chamber at the input end to a designated sensor bank. By using the shape of the PCBs to create flow pathways, additional components are not needed (e.g., tubing to route gases/vapors), thus beneficially conserving space requirements in the plug and saving cost.

In this embodiment, the acetic acid sensor chamber 430 is the first layer above the input end 415, and thus the gases only need to travel up one level from the input end 415. Gases from the storage container enter the input end 415 of the plug 400, and if any acetic acid is present, it will selectively be allowed to enter input chamber 418-1, represented schematically in FIG. 4B as a mesh pattern. The input chamber 418-1 is covered with a filter that primarily allows acetic acid to enter that chamber. Gas/vapor in input chamber 418-1 travels through opening Q1 (FIGS. 4A and 4C), which is in fluid communication with the acetic acid sensor chamber 430. For example, opening Q1, which is an open space created between housing 410 and an edge of the PCB in sensor chamber 430, is aligned with the input chamber 418-1 below sensor chamber 430.

Other gases that have entered the plug through the other input chambers 418-2, 418-3 and 418-4 (FIG. 4B) are blocked from being detected by the acetic acid sensor chamber 430 by walls 482 in FIG. 4A. Walls 482, which correspond to walls 382 of FIG. 3A, extend along three edges of the sensor chamber 430 except for the edge adjacent to the Q1 open space. The walls 482 have a height that fills the vertical space between the PCB of sensor chamber 430 and the PCB of sensor chamber 440 above sensor chamber 430, thus forming an enclosed volume around the acetic acid sensor bank 435. The enclosed volume only allows gas from the acetic acid sensor chamber 430 to access the acetic acid sensor bank 435. In subsequent layers above the acetic acid sensor layer the Q1 opening is blocked (Q1' closed areas of FIG. 4C), preventing the acetic acid from traveling to the other sensors. The Q1' area may be configured as a closed space on the sensor chamber 440 layer and other subsequent layers due to the PCB material (i.e., base or substrate of the PCB) being shaped to fill the space (e.g., not being cut off), or by another material being inserted to fill the Q1' space.

The next sensor bank 445 is in phenol/guaiacol sensor chamber 440, which is in fluid communication with the input chamber 418-3 of input end 415. The mesh opening of the phenol input chamber 418-3 is covered by a filter that primarily allows phenols, including guaiacol, to pass through. That is, the filter is made of a material that selectively permits phenols to pass through, while blocking or substantially preventing other substances from traversing the filter. Gas flows from the phenol input chamber 418-3 through the Q3 openings of sensor chambers 430 and 440 (FIGS. 4A, 4C). The Q3 openings form a flow pathway between the input chamber 418-3 and the sensor chamber 440. Input chamber 418-3 is aligned with the Q3 open spaces. For the phenol/guaiacol sensor chamber 440, the Q1' closed space along with walls 484 on the Q2 and Q4 sides of the PCB prevent non-phenol substances from entering the phenol/guaiacol sensor chamber 440. The walls 484 have a height that fills the vertical space between the PCB of sensor chamber 440 and the PCB of sensor chamber 450 above it. The walls 484 and the housing 410 along the Q1' edge form side walls for the phenol/guaiacol sensor chamber 440, with gas carrying phenol/guaiacol particles entering phenol/guaiacol sensor chamber 440 from the Q3 channel. Above the phenol/guaiacol sensor layer, the Q3 openings are blocked as shown by the Q3' closed space of sensor chambers 450 and 460, to prevent phenol particles from proceeding to the sensor banks above the phenol bank. The printed circuit board of sensor bank 445 forms a boundary of the sensor chamber 440, with the flow pathway between input chamber 418-3 and sensor chamber 440 traversing the open space Q3 between the housing 410 and an edge of the printed circuit board of sensor bank 445.

The third sensor bank 455 is for $H_2$ or $HO_2$, indicated by the $H_2/HO_2$ sensor chamber 450. $H_2$ and/or $HO_2$ gases enter plug 400 through input chamber 418-4 at input end 415 (FIG. 4B) and travel through a flow pathway that includes openings Q4 in sensor chambers 430, 440 and 450 (FIGS. 4A, 4C). The input chamber 418-4 is aligned with the Q4 openings. The mesh opening of the $H_2/HO_2$ input chamber 418-4 is covered by a filter that is permeable primarily by $H_2$ and/or $HO_2$. That is, the filter selectively allows $H_2$ and/or $HO_2$ to pass through while blocking other substances from entering. The Q4 openings are open at every layer except the last layer—sensor chamber 460—which is for $SO_2$. Wall 486 seals the Q2 opening from sensor chamber 450, by having a height that extends from the PCB of sensor chamber 450 to the PCB of sensor chamber 460. The housing 410 forms the remainder of the perimeter of the $H_2/HO_2$ sensor chamber 450.

For the uppermost $SO_2$ sensor chamber 460, gas flows into input chamber 418-2 through a filter that allows $SO_2$ to enter while preventing or greatly limiting other substances from passing. The $SO_2$ gas continues through the Q2 areas which are open in every sensor chamber 430, 440, 450 and 460, to reach the $SO_2$ sensor bank 465. In $SO_2$ sensor chamber 460, areas Q1', Q3' and Q4' are all closed, either by the presence of the PCB of sensor chamber 460 or by another material (e.g., a plastic piece, or epoxy) filling those spaces. Housing 410 serves as side walls for the perimeter of the $SO_2$ sensor chamber 460. The upper surface 470 of $SO_2$ sensor chamber 460 may be the PCB of another sensor layer (e.g., for another analyte or for environmental measurements), or a PCB for processing components (e.g., PCB 370 of FIG. 3A), or may be the housing 310 or ring 322 if no more circuit boards are included above sensor chamber 460.

Figure 5:
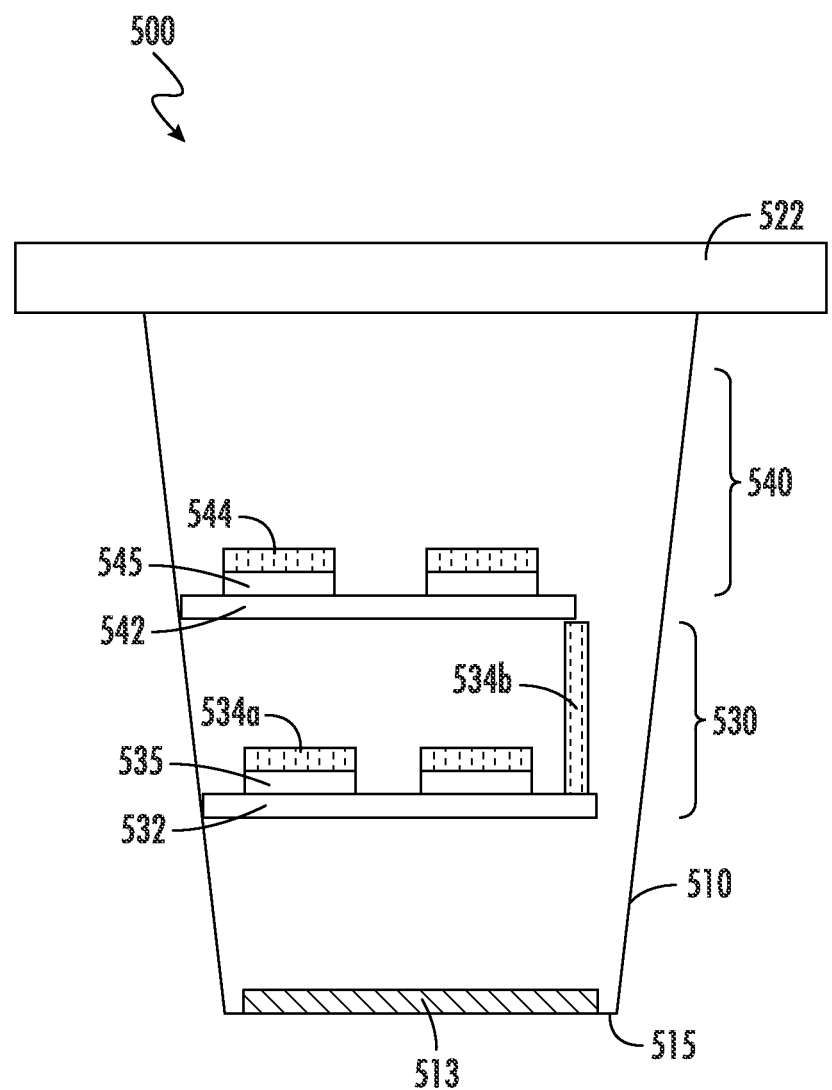
FIG. 5 is a cross-sectional schematic of a sensor plug device, in accordance with some embodiments.

In an alternative embodiment of the plugs 300 and 400, in FIG. 5, a plug 500 has specific filters are placed between the input end and the sensors themselves, but not necessarily at the input end. In plug 500, membrane 513 at the input end 515 may be a liquid-impermeable membrane, allowing gases/vapors to enter in a non-specific manner. That is, all gases/vapors (and substances carried by the gases) can pass through the membrane 513 at the input end 515. In one embodiment, a single membrane 513 can cover a single mesh opening array that spans the input end, rather than multiple mesh openings as in FIG. 3B. Thus, individual input chambers are not required. A first sensor chamber 530 inside housing 510 is bounded by printed circuit board 532, printed circuit board 542 above PCB 532, and housing 510 around the lateral sides. Sensors 535 are mounted on PCB 532. In one embodiment, substance-specific filters 534a are placed on the sensors 535 themselves, in the sensor bank. In another embodiment, instead of placing filters on the sensors, substance-specific filter 534b is placed at an entrance to the sensor chamber 530, such as by forming a vertical wall between PCB 532 and PCB 542. A second sensor chamber 540 inside housing 510 is bounded at a lower end by PCB 542, at an upper end by ring 522 (which may instead be a portion of the housing 510), and laterally by housing 510. Sensors 545 are mounted on PCB 542 and have substance-specific filters 544 covering the sensors 545. Two sensor chambers are shown in this embodiment, but other numbers of chambers, such as one sensor chamber or more than two, are possible.

Figure 6:
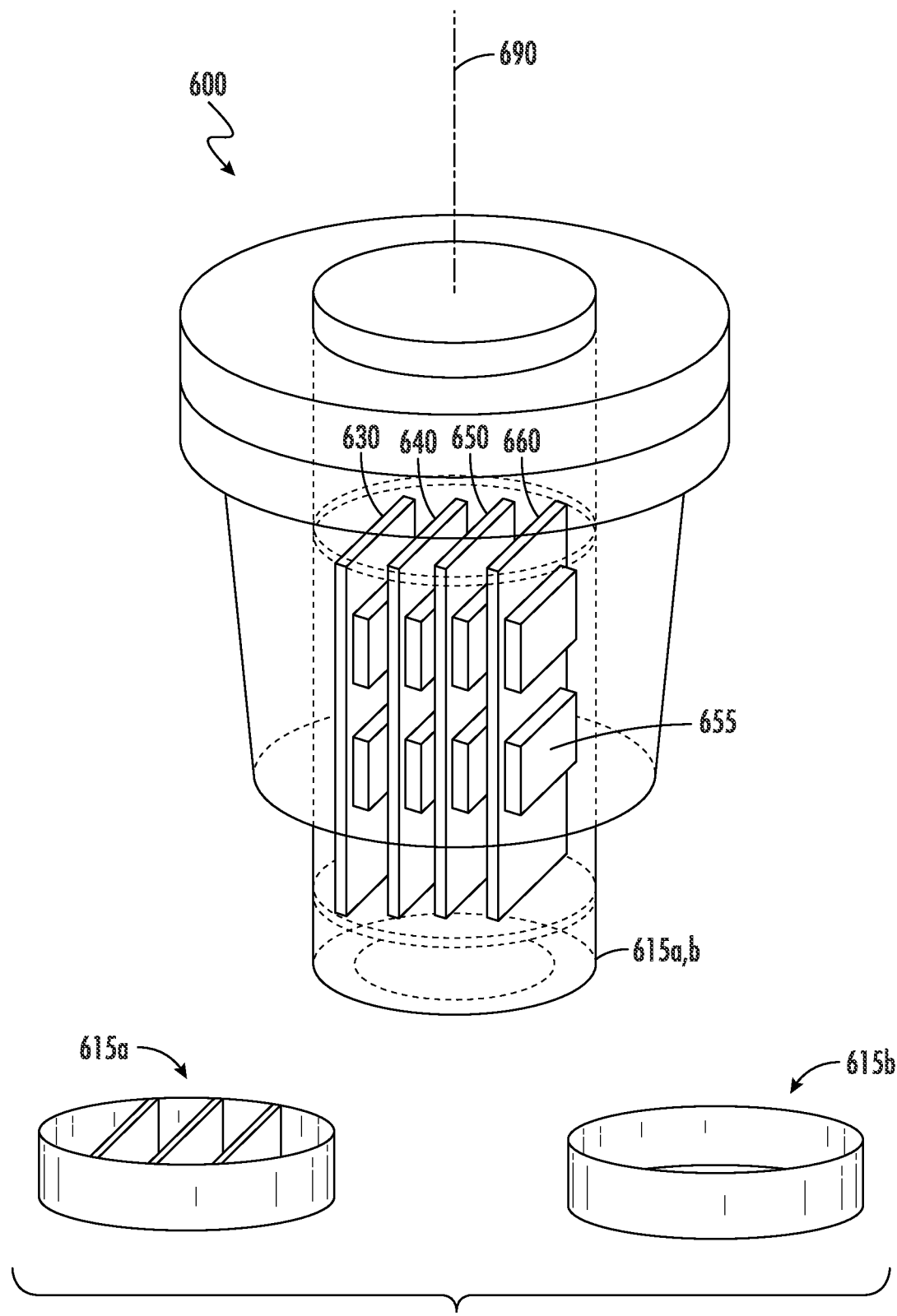
FIG. 6 is an isometric diagram of another sensor plug device, in accordance with some embodiments.

FIG. 6 is an isometric schematic of an embodiment of a plug 600 that has four sensor banks 630, 640, 650 and 660. In this embodiment, the sensor banks are arranged vertically, aligned along a vertical axis 690. That is, the sensor banks are stacked along a horizontal direction instead of vertical (longitudinal) axis 690 as in previous embodiments. In one embodiment, the input end can be multi-chambered as shown by input end 615a. The input end 615a is sectioned into individual input chambers similar to input end 415 of FIG. 4A, with each having a different substance-specific filter. The input chambers of input end 615a are parallel to each other in this embodiment, rather than being radially arranged as in FIG. 4A (input chambers 418). Input end 615a,b can also be covered by a liquid-impermeable membrane, allowing gas flow to enter the plug 600 but not liquids. Each individual input chamber of input end 615a can be in fluid communication with a corresponding sensor chamber holding one of the sensor banks 630, 640, 650 or

660. In another embodiment, the plug 600 has an input end 615*b* that is not partitioned but instead can allow gases to enter in a non-specific manner. In such an embodiment, filters can be placed at other locations between the input end and the sensors as described in relation to FIG. 5. For example, substance-specific filters can be placed on sensor 655 or at an entrance to the sensor chamber for sensor bank 650.

The present sensor plug devices beneficially filter out non-target gases from entering the plug, thus improving accuracy of detection. In some embodiments, the sensor PCBs and their arrangements in the housing are configured to uniquely allow each gas with its target analyte to flow only to the corresponding sensor PCB. This further improves accuracy of the measurements by reducing non-desired substances from interfering with detection of the target substance by a specific sensor.

Figure 7A:
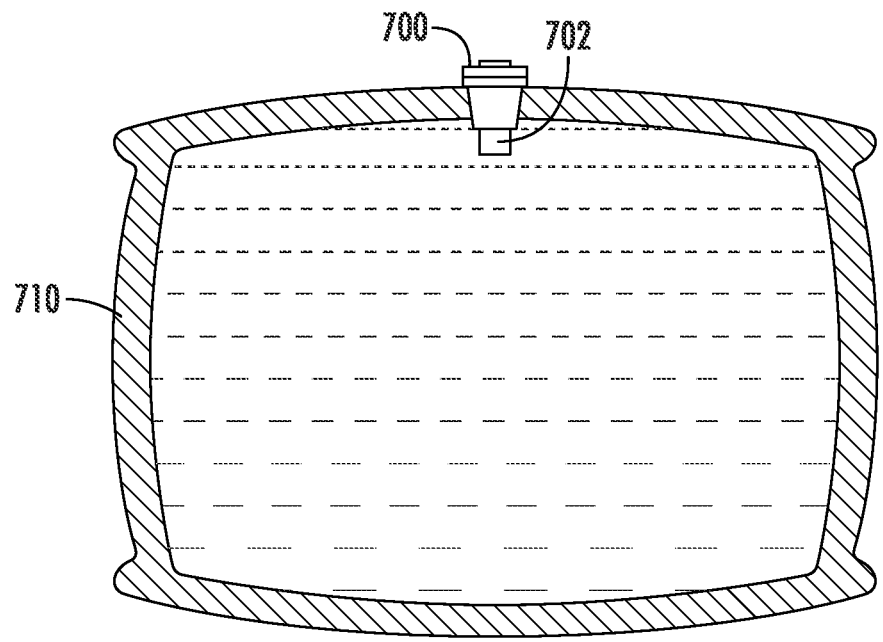
FIGS. 7A-7B are cross-sectional views of a barrel fully filled with liquid and after some evaporation of the liquid, respectively, in accordance with some embodiments.
Figure 7B:
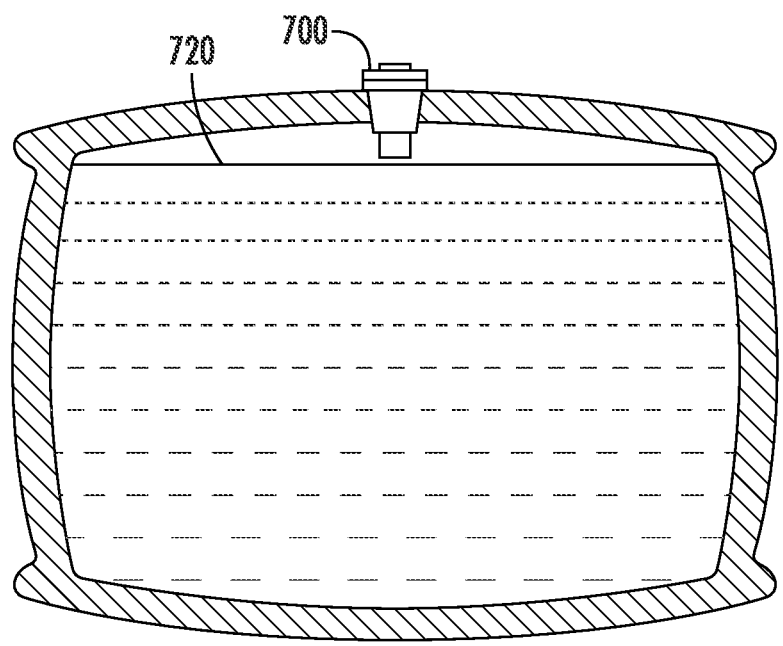

FIGS. 7A-7B demonstrate using a plug 700 to detect a decrease in the liquid level within the storage container 710 due to evaporation. For wine stored in barrels, for instance, drier conditions tend to make the barrels evaporate more water, strengthening the spirit. However, in higher humidity, more alcohol than water will evaporate, therefore reducing the alcoholic strength of the product. Thus, it is valuable for winemakers to know when a barrel needs to be topped off due to evaporation. In FIG. 7A, the barrel is filled to the top of the barrel initially. Wine naturally evaporates over time, which is a normal part of the aging process. The plug 700 has an additional length 702 at the bottom end, making the plug 700 taller than the previous embodiments. As the wine evaporates as shown in FIG. 7B, the additional length 702 enables the plug 700 to sense the decreased liquid level 720. The decreased liquid level 720 creates a vacuum inside the barrel, which impacts the ability for gas to enter the plug 700. This will cause a shift in the sensor readings of the plug 700, which can be calibrated for. Because of the vacuum, the sensors will shift in their readings and give an indication through that shift that the barrel needs to be topped off, which is valuable indicator to winemakers. A processor (e.g., central processor 240 of FIG. 2) associated with plug 700 can track how many days it takes for the wine to evaporate to a level below the bottom of the plug 700 and then calculate a rate per day of evaporation since the climate controls at the warehouse or other storage area are typically kept consistent. With the rate per day established, the winemaker can then estimate how much will be evaporating in the future, thereby providing the winemaker with clarity as to where the wine level is at any moment going forward and when to add more wine or top off the barrel.

Although smart plugs for monitoring contents of alcoholic liquids are known, none exist for detecting smoke taint. Devices of the present disclosure uniquely utilize sensors specifically designed to detect guaiacol and other phenols as indicators of smoke taint. When grapevines are exposed to smoke, the grapevines absorb volatile phenols from the smoke. The grapevines metabolize the volatile phenols through glycosylation, forming phenolic glycosides. These non-volatile glycosides become cleaved and release free volatile phenols during fermentation and aging of the wine, consequently imparting smoky or ashy flavors to the wine. Volatile phenols that are known to contribute to smoke taint are guaiacol (including free guaiacol, 1-methylguaiacol, 4-methylguaiacol), cresols (m-cresol, o-cresol and p-cresol), syringol and trans-resveratrol. Conventional methods use liquid samples of the wine or grapes to assess the presence of these phenolic substances.

Figure 8:
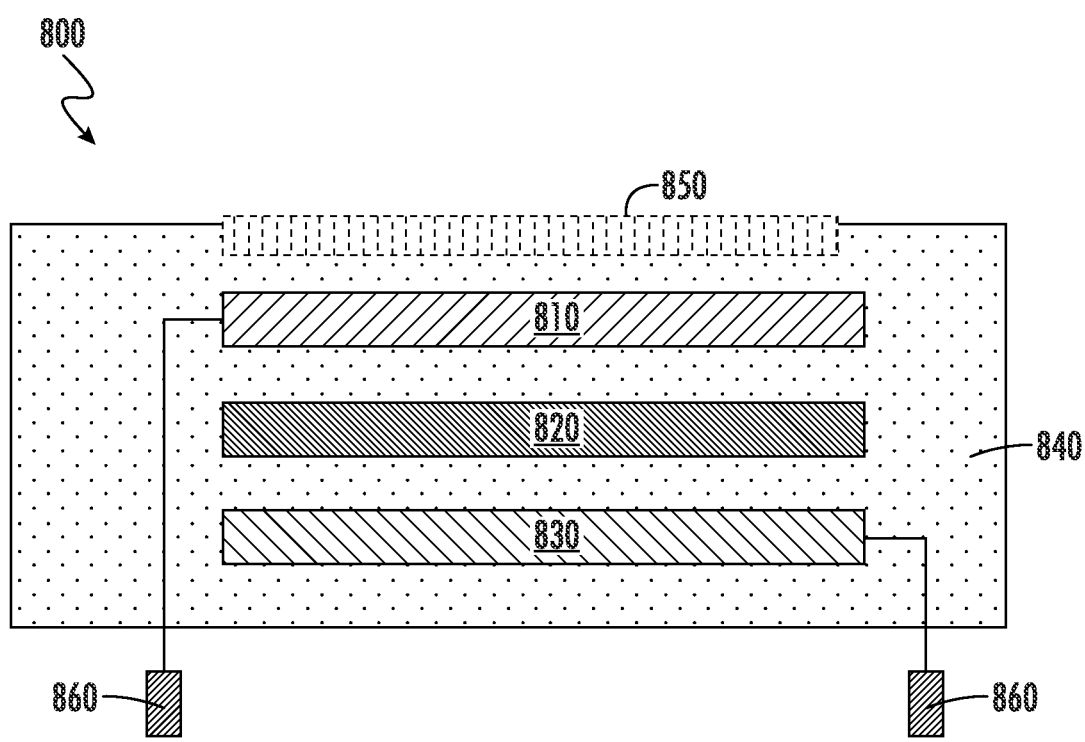
FIG. 8 is a schematic of an electrochemical sensor, in accordance with some embodiments.

In some embodiments, the sensors of the present plug devices are amperometric gas sensors (e.g., some or all of the sensors in the sensor banks of plugs 300, 400, 500, 600), which are electrochemical sensors that produce a current based on a volumetric fraction of a substance in a gas. By using electrochemical sensing of the gases or vapors entering the plug devices, results can be obtained much faster than with wet chemistry methods, where liquid samples must be physically extracted and analyzed in laboratory testing. The sensors may be an electrochemical sensor 800 as shown schematically in the cross-sectional view of FIG. 8. Electrochemical sensors generally include a working 810 electrode (also referred to as a sensing electrode), reference electrode 820 and counter electrode 830, where the electrodes 810, 820 and 830 are surrounded by an electrolyte 840. Gases enter the sensor through a porous barrier 850 (e.g., capillary diffusion barrier) and cause a reaction at the working electrode 810 to generate a current. The working electrode is configured to react with the target substance (e.g., particle, ion, compound, molecule) that is to be identified. The target gas causes a reaction (e.g., oxidation/reduction reaction) at the working electrode, thus generating an amperometric signal to indicate presence of the target substance. The counter electrode 830 completes the circuit with the working electrode 810, allowing electrons to enter or leave the electrolyte 840 in an equal amount and opposite direction of the electrons involved with the reaction at the working electrode 810. The reference electrode 820 provides a reference potential (i.e., approximately constant voltage level) against which the working electrode 810 is compared. The gas sensor 800 may be operated using a potentiostatic circuit (not shown) coupled to the sensor pins 860, where the potentiostatic circuit establishes a fixed bias potential between the working electrode 810 and reference electrode 820. The working electrode current is converted to a voltage by a first operational amplifier (op-amp), and a second op-amp generates a voltage at the counter electrode to supply a current that is equal and opposite of the working electrode.

The plug devices of the present disclosure include sensors that are specially designed to detect volatile phenols related to smoke taint, such as guaiacol and 4-methylguaiacol. In some embodiments, electrode materials may be customized to react with guaiacol and other phenols. In some embodiments, the plurality of sensors in a sensor bank to detect a smoke taint compound (e.g., the phenol/guaiacol sensor bank 445 of FIG. 4A) may be a variety of types of sensors rather than multiple identical sensors. The variety of detectors may be used to triangulate the presence of guaiacol and other smoke taint substances, such as by using two or three sensors operating at different biases. A combination of sensors (e.g., sub-sensors in a smoke taint sensor) enables the plug device to deduce the presence of the particles of interest. For example, in some embodiments an overall presence of various substances (e.g., particles, ions, and/or molecules) can be measured, and then those that are known not to be phenols are subtracted out from the measurements to leave possible phenols as the remaining substances. In some embodiments, substances having chemical compounds related to phenols can be detected (e.g., particles containing H and C, or certain C—H bonds), and the device can deduce the presence of smoke taint compounds (e.g., guaiacol and/or 4-methylguaiacol and/or cresols) from those measurements.

Figure 9:
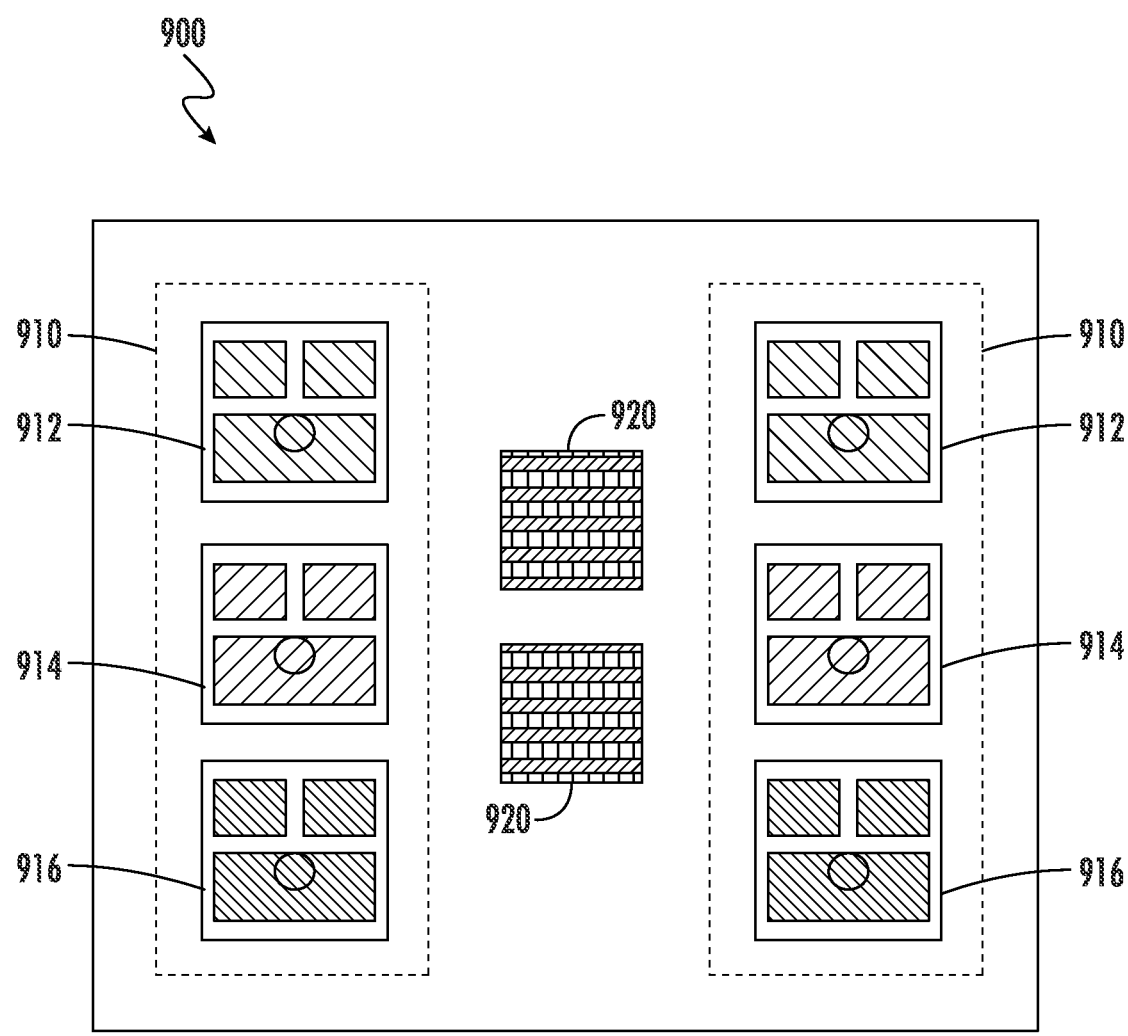
FIG. 9 is a schematic of a sensor bank for detecting a smoke taint compound, in accordance with some embodiments.

FIG. 9 is a schematic of a sensor bank 900 for detecting a smoke taint compound, in accordance with some embodiments. For example, sensor bank 900 can be configured to detect one or more smoke taint compounds (e.g., molecules, ions, particles), such as smoke-derived volatile phenols including guaiacol, 4-methylguaiacol, syringol, o-cresol, m-cresol, p-cresol and/or trans-resveratrol. Two sensors 910 are shown, each having three sub-sensors 912, 914 and 916 in this embodiment. Other embodiments can have different numbers of sub-sensors, such as one, two or more than three. The sub-sensors 912, 914 and 916 can be fabricated as one sensor (sensor 910) or can be mounted as separate components onto sensor bank 900. Processing circuit boards 920 can also be included on sensor bank 900 to perform calculations on the measurements collected from the sub-sensors. Alternatively, processing circuit boards 920 can be located elsewhere in the plug device, such as on a different printed circuit board.

In some embodiments, the individual sub-sensors 912, 914 and 916 sense different substances from each other, to provide responses to a variety of substances (e.g., molecules, particles or ions) from which the presence of target smoke taint compounds can be derived. Measurements from individual sub-sensors of the plurality of sub-sensors can be used to determine a presence of phenols, to detect a smoke taint compound. For example, sub-sensor 912 can be an air quality sensor, and sub-sensors 914 and 916 can be sensors for substances different from or overlapping those of sub-sensor 912 (e.g., targeting ethanol, sulfur dioxide, hydrogen or a combination of gases/particles). In such an embodiment, target gases for air quality sub-sensor 912 may be, for example, sulfides, alcohol, ammonia, and or carbon monoxide. Sub-sensor 914 may be a hydrogen ($H_2$) sensor, and sub-sensor 916 may be an ethanol (EtOH) sensor. Sub-sensors 912, 914 and 916 may also have cross-sensitivities (i.e., detection of interfering gases), such as to one or more of carbon monoxide (CO), hydrogen sulfide ($H_2S$), ozone ($O_3$), nitrogen dioxide ($NO_2$), sulfur dioxide ($SO_2$), ethanol (EtOH), nitric oxide (NO), chlorine, heptane, ammonia ($NH_3$), methane, and saturated hydrocarbons. Measurements of the target gases and cross-sensitivities from the sub-sensors can be compared to each other to derive the presence of another substance. For example, measurement of $H_2$ from the $H_2$ sub-sensor 914, can be used to subtract $H_2$ from the air quality measurements of sub-sensor 912 and consequently derive the presence of phenol substances from sub-sensor 912. Other types of sensors can be used for sub-sensors 912, 914 and 916, such as ozone detectors, $SO_2$, or air quality sensors that sense other combinations of gases/particles. In embodiments, measurements from the individual sub-sensors are used to determine a presence of guaiacol, 4-methylguaiacol and/or other volatile phenols related to smoke taint.

More than one of each type of sub-sensor 912, 914, 916 can be included in sensor bank 900, such as two or three of each type. In such an example, the sub-sensors can be electrochemical sensors that are operated at varying biases (voltage potentials) to detect different analytes. In some embodiments, an individual sub-sensor can take measurements at different voltage potentials at different times, and those measurements cross-correlated (e.g., comparing measurements taken from one sub-sensor 912 at three potentials). In some embodiments, multiple sub-sensors of one type can be operated at different biases from each other (e.g., three sub-sensors 912 each at a different potential from each other), where measurements from the individual sub-sensors are used to determine a presence of the smoke taint compound. Using various biases can encourage or speed up certain chemical reactions on the sensor, which can help identify certain analytes specifically. An anodic bias (positive potential) encourages oxidation, while a cathodic bias (negative potential) encourages reduction. Consequently, compounds that are oxidizable will generate electrochemical signals at those oxidation potential levels. As one example, different C—C double/aromatic bonds and C—O bonds may react at different potentials. Thus, using different voltages (biases) on the sub-sensors can distinguish the smoke-derived phenols from each other.

Various quantities can be measured by the devices of the present disclosure in addition to or instead of those mentioned above. Environmental factors include external (outside the storage container) and internal (inside the storage container) factors, such as external temperature, external humidity, internal temperature, internal humidity, and internal pressure. Monitoring internal pressure can be helpful during fermentation and other uses when yeast is very active, especially early in the aging process. In one example, micro-electromechanical sensors (MEMS) pressure sensors can be included inside the plug (e.g., on PCB 370 of FIG. 3A) to measure internal pressure. Substances measured inside the storage container can include one or more of: carbon dioxide ($CO_2$), oxygen, pH, acetic acid, sulfur dioxide ($SO_2$), alcohol (e.g., ethanol), malic acid and sugar.

In some embodiments, redox potential, to measure redox or a change in the oxidation state at an atomic level, is another value that can be measured to detect smoke taint compounds or other substances. Redox potential can be measured by a platinum detection surface on a sensor or other technique.

In some embodiments, measurements of the liquid in the storage container can be taken in addition to gas/vapor measurements as described elsewhere in this disclosure. Liquid measurements can be taken by sensors located on a surface of the plug that will be immersed in the liquid. For example, a sensor coated with platinum or other noble metal (e.g., gold) can be present on the exterior surface of the input end of the plug (e.g., on the compartment walls 313 of FIG. 3B), to be submerged in the liquid stored in the container. In other examples, optical sensors (e.g., infrared or near-infrared), ion sensors, absorption sensors, and/or electrical conductivity sensors can be incorporated inside or on an exterior surface of the plug, where measurements from these sensors can be used in conjunction with electrochemical gas sensing measurements to determine the presence of smoke taint compounds and/or other substances. In further examples, heated metal oxide (HMOx) sensors can be used instead of or in addition to the electrochemical gas sensors described herein. The various sensors can be operated at varying operating conditions, such as various optical wavelengths or various alternating current frequencies, to determine specific substances based on the responses. In another example, a catalytic active species can be identified by an electrode that is immersed in the liquid and operated at a controlled potential. If the catalytic active species is present, a signal will be produced at an electrical current related to amount of potential applied.

In some embodiments, acetic acid (ethanoic acid $CH_3COOH$), which can contribute to wine flavors due to its vinegar aromas, can be detected by a specific acetic acid sensor or by cross-referencing a combination of sensors and comparing results to arrive at an accurate measurement. That is, in some embodiments an acetic acid sensor can comprise sub-sensors as described in relation to the phenol sensor of FIG. 9. For instance, an air quality sensor, an alcohol sensor and other sensors (e.g., aromatics, nitrogen oxides) can be used as sub-sensors of an acetic acid sensor, to arrive at a composite value that indicates the amount of acetic acid present.

In an embodiment for aging whiskey, sensors can be included for sugar, methanol or butane. In some embodiments, the presence of methanol can be derived from a methane sensor or by several sensors that are biased at different potentials to compare results. In some embodiments, sugar can be measured by an ultrasonic sensor.

In general embodiments, various types of sensors may be utilized in the devices of the present disclosure. In some embodiments, the sensors may be electrochemical sensors, such as printed gas sensors (e.g., fabricated by screen printing). In some embodiments, the sensors can be non-PCB sensors sized to fit into the plug, where the boards of the sensor chambers include adapters to provide an interface for the sensor. In some embodiments, the sensors can be ultrasonic sensors for gas and particles, such as for sugar.

The various sensors in the plug—whether for guaiacol, $SO_2$ or other—may also be specifically designed regarding size and/or power requirements for the present plug devices. Individual sensors may be designed to be, for example, less than 1 $cm^2$ which is smaller than conventional sensors. Smaller sizes enable a plurality of sensors to fit into each sensor bank and also reduce the power requirements of the plug, thus elongating battery life.

The filters of the present plug devices may also be uniquely customized in accordance with some embodiments, such as to detect guaiacol or other smoke taint compounds. As described above, each chamber of the input end of the plug or each sensor bank may have a filter to restrict non-target gases from contaminating the readings of the sensor bank. The filters may operate by absorbing substances (e.g., gas, particles, ions) other than the desired substance. By incorporating substance-specific filters in the plug, noise from other substances is reduced or eliminated, thus improving accuracy of detection. Although filters are known in the industry to be used in gas sensors, no filters currently exist for smoke-related phenols or for guaiacol in particular. Embodiments may include tailoring the fiber material of the filter (e.g., glass fiber, polytetrafluoroethylene or other), fiber thickness, additives and/or catalysts in the filter to enable primarily the substance of interest (e.g., guaiacol, phenols) to pass through. In another embodiment, an $SO_2$ filter may uniquely utilize sintered glass fiber, in which gas fiber is sintered or fused into a material at microscopic levels to allow only $SO_2$ to permeate through the filter. An $H_2$ filter may involve novel approaches, such as using non-conventional materials sintered into a dense state. Alcohol/ethanol filters may use an elastomeric material such as a rubber or plastic compound. In some embodiments, the phenol filters may also utilize an elastomeric material.

The data from the smoke taint devices can beneficially be used by producers of the wines, spirits, or other liquids to improve the quality of their products. Embodiments include data usage for seasonal clarity and future planning, such as to compare one season's batch to the next, allowing improved control and planning. Data can also be used to verify the quality of a wine or spirit, looking for changes during aging as indicated by the recorded data. As an example, data can be used to certify that the wine has been purely produced during the aging process, or to verify the identity of a high-end bottle to a collector to prevent counterfeiting. In other embodiments, data from vineyards can be used for insurance claim purposes, such as to document damage of that year's harvest from smoke contamination. The collected information can be reported on a web application, allowing multiple users to access the data and to check for alerts.

In some embodiments, a plug for a container for storing liquids (e.g., aging wine or spirits) includes a housing (e.g., housing 310 of FIG. 3A) and an input end (e.g., input end 315 of FIG. 3A) at one end of the housing, the input end having a plurality of chambers (e.g., input chambers 418 of FIG. 4A). A first sensor is in a first sensor chamber (e.g., sensor bank 445 in sensor chamber 440 of FIG. 4A) inside the housing, the first sensor being configured to detect guaiacol. A first filter (e.g., filter 314 of FIG. 3A) is near the input end of the plug, where the first filter selectively allows phenols including guaiacol to enter a first input chamber (e.g., input chamber 418-3 of FIG. 4B) of the plurality of chambers. A first flow pathway (e.g., channel through Q3 openings of FIGS. 4A and 4C) is between the first sensor chamber and the first input chamber. A second sensor is in a second sensor chamber (e.g., sensor bank 435, 455 or 465 of sensor chamber 430, 450 or 460, respectively, of FIG. 4A) inside the housing, the second sensor being configured to detect a second substance different from the phenols. A second filter (e.g., filter 314 of FIG. 3A) is near the input end of the plug, wherein the second filter selectively allows the second substance to enter a second input chamber (e.g., input chamber 418-1, 418-4 or 418-2 of FIG. 4B) of the plurality of chambers. A second flow pathway (e.g., channel through Q1, Q4 or Q2 openings of FIGS. 4A and 4C) is between the second sensor chamber and the second input chamber.

In some embodiments, the first sensor is mounted on a first printed circuit board that is shaped to create the first flow pathway, and the second sensor is mounted on a second printed circuit board that is shaped to create the second flow pathway, the second flow pathway being separated from the first flow pathway. The first printed circuit board may be shaped to create an open space between a first edge of the first printed circuit board and the housing, where the first flow pathway traverses the open space. The first sensor chamber may have boundaries defined by i) the first printed circuit board, ii) the second printed circuit board, and iii) at least one of: the housing or a wall that extends between the first printed circuit board and the second printed circuit board. The first printed circuit board and the second printed circuit board may be spaced apart from each other along an axis of the housing, where the axis may be a longitudinal axis of the housing.

In some embodiments, the plug includes a plurality of the second sensors and a processor that averages data sensed by the plurality of second sensors. In some embodiments, the first sensor comprises a plurality of sub-sensors, individual sub-sensors of the plurality of sub-sensors detect different substances from each other, and measurements from the individual sub-sensors are used to determine a presence of at least one of the phenols. In some embodiments, the first sensor comprises a plurality of sub-sensors, individual sub-sensors of the plurality of sub-sensors operate at different biases from each other, and measurements from the individual sub-sensors determine a presence of at least one of the phenols.

In some embodiments, the plug includes a membrane over the input end, where the membrane prevents liquid from entering the plug. In some embodiments, the plurality of chambers is arranged radially around a longitudinal axis of the housing.

In some embodiments, a plug for a container for storing liquid includes a housing (e.g., housing 310 of FIG. 3A) and an input end (e.g., input end 315 of FIG. 3A) at an end of the housing, the input end having a liquid-impermeable membrane (e.g., a membrane as part of or in addition to filter 314 of FIG. 3A) that allows gas flow to pass. A first sensor is in a first sensor chamber inside the housing (e.g., sensor bank 445 in sensor chamber 440 of FIG. 4A), the first sensor being configured to detect a smoke taint compound. A first filter (e.g., filter 314 of FIG. 3A or filters 534a,b of FIG. 5) is between the input end and the first sensor, wherein the first filter selectively allows phenols to pass through. A second sensor is in a second sensor chamber (e.g., sensor bank 435, 455 or 465 of sensor chamber 430, 450 or 460, respectively, of FIG. 4A) inside the housing, the second sensor being configured to detect a second substance different from the smoke taint compound. A second filter (e.g., filter 314 of FIG. 3A or filters 534a,b of FIG. 5) is between the input end and the second sensor, where the second filter selectively allows the second substance to pass through.

In some embodiments, the first filter is in a first input chamber at the input end, the first input chamber being in fluid communication with the first sensor chamber via a first flow pathway; the second filter is in a second input chamber at the input end, the second input chamber being in fluid communication with the second sensor chamber via a second flow pathway; and the first flow pathway is separate from the second flow pathway.

In some embodiments, the first sensor is mounted on a first printed circuit board that is shaped to create a first flow pathway between the input end and the first sensor chamber; and the second sensor is mounted on a second printed circuit board that is shaped to create a second flow pathway between the input end and the second sensor chamber. In some embodiments, the first sensor is mounted on a first printed circuit board that forms a boundary of the first sensor chamber; and a first flow pathway between the input end and the first sensor chamber traverses an open space between an edge of the first printed circuit board and the housing.

In some embodiments, the smoke taint compound is guaiacol or 4-methylguaiacol. In some embodiments, the second substance is acetic acid, sulfur dioxide, or hydrogen. In some embodiments, the first sensor comprises a plurality of sub-sensors; individual sub-sensors of the plurality of sub-sensors detect different substances from each other; and measurements from the individual sub-sensors are used to determine a presence of the smoke taint compound.

In some embodiments, the first sensor comprises a plurality of sub-sensors; individual sub-sensors of the plurality of sub-sensors operate at different biases from each other; and measurements from the individual sub-sensors are used to determine a presence of the smoke taint compound. In some embodiments, the first sensor comprises a plurality of sub-sensors; and measurements from individual sub-sensors of the plurality of sub-sensors determine a presence of phenols, to detect the smoke taint compound.

Figure 10:
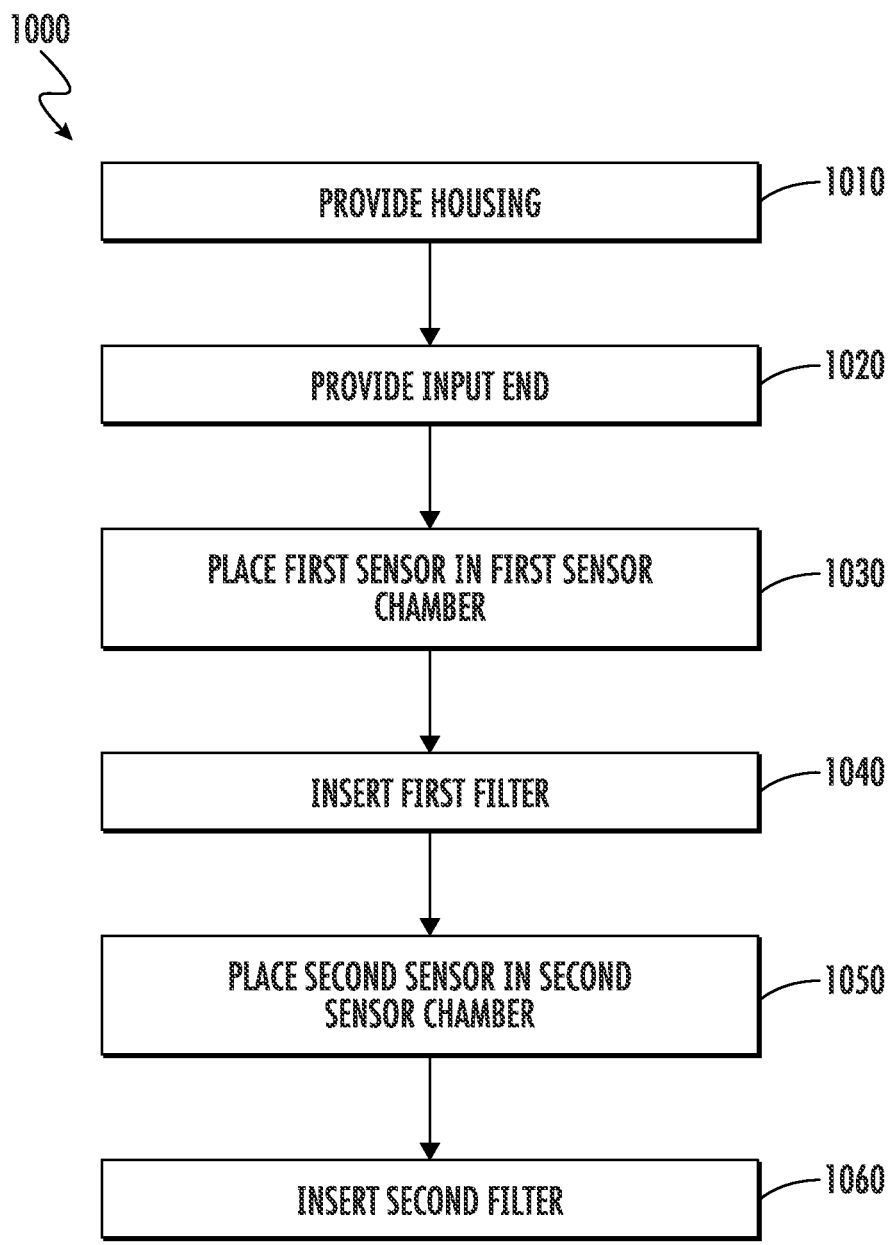
FIG. 10 is a flowchart of methods for manufacturing sensor plug devices, in accordance with some embodiments.

Methods for making sensor plug devices in accordance with the present disclosure are represented by the flowchart 1000 of FIG. 10. In some embodiments, methods for making a plug for a container for storing liquid include providing a housing (step 1010) and an input end (step 1020) at an end of the housing, the input end having a liquid-impermeable membrane that allows gas flow to pass through. In step 1030, a first sensor is placed in a first sensor chamber in the housing, the first sensor being configured to detect a smoke taint compound. In step 1040, a first filter is inserted between the input end and the first sensor, where the first filter selectively allows phenols to pass through. In step 1050, a second sensor is placed in a second sensor chamber inside the housing, the second sensor being configured to detect a second substance different from the smoke taint compound. In step 1060, a second filter is inserted between the input end and the second sensor, where the second filter selectively allows the second substance to pass through. The plugs manufactured according to flowchart 1000 include embodiments described in this disclosure such as different chamber configurations, input ends with filters and membranes in various locations, various sensor types, and different combinations of substances detected by the sensors.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A plug for a container for storing liquid, the plug comprising:
    a housing;
    an input end at one end of the housing, the input end having a plurality of chambers;
    a first sensor in a first sensor chamber inside the housing, the first sensor being configured to detect guaiacol;
    a first filter near the input end of the plug, wherein the first filter selectively allows phenols including the guaiacol to enter a first input chamber of the plurality of chambers;
    a first flow pathway between the first sensor chamber and the first input chamber;
    a second sensor in a second sensor chamber inside the housing, the second sensor being configured to detect a second substance different from the phenols;
    a second filter near the input end of the plug, wherein the second filter selectively allows the second substance to enter a second input chamber of the plurality of chambers; and
    a second flow pathway between the second sensor chamber and the second input chamber.

2. The plug of claim 1, wherein:
    the first sensor is mounted on a first printed circuit board that is shaped to create the first flow pathway; and
    the second sensor is mounted on a second printed circuit board that is shaped to create the second flow pathway, the second flow pathway being separated from the first flow pathway.

3. The plug of claim 2, wherein:
    the first printed circuit board is shaped to create an open space between a first edge of the first printed circuit board and the housing; and
    the first flow pathway traverses the open space.

4. The plug of claim 2, wherein the first sensor chamber has boundaries defined by i) the first printed circuit board, ii) the second printed circuit board, and iii) at least one of: the housing or a wall that extends between the first printed circuit board and the second printed circuit board.

5. The plug of claim 2, wherein the first printed circuit board and the second printed circuit board are spaced apart from each other along an axis of the housing.

6. The plug of claim 5, wherein the axis is a longitudinal axis of the housing.

7. The plug of claim 1, further comprising:
a plurality of the second sensors; and
a processor that averages data sensed by the plurality of the second sensors.

8. The plug of claim 1, wherein:
the first sensor comprises a plurality of sub-sensors;
individual sub-sensors of the plurality of sub-sensors detect different substances from each other; and
measurements from the individual sub-sensors are used to determine a presence of at least one of the phenols.

9. The plug of claim 1, wherein:
the first sensor comprises a plurality of sub-sensors;
individual sub-sensors of the plurality of sub-sensors operate at different biases from each other; and
measurements from the individual sub-sensors determine a presence of at least one of the phenols.

10. The plug of claim 1, further comprising a membrane over the input end, wherein the membrane prevents liquid from entering the plug.

11. The plug of claim 1, wherein the plurality of chambers is arranged radially around a longitudinal axis of the housing.

12. A plug for a container for storing liquid, the plug comprising:
a housing;
an input end at an end of the housing, the input end having a liquid-impermeable membrane that allows gas flow to pass through;
a first sensor in a first sensor chamber inside the housing, the first sensor being configured to detect a smoke taint compound;
a first filter between the input end and the first sensor, wherein the first filter selectively allows phenols to pass through;
a second sensor in a second sensor chamber inside the housing, the second sensor being configured to detect a second substance different from the smoke taint compound; and
a second filter between the input end and the second sensor, wherein the second filter selectively allows the second substance to pass through.

13. The plug of claim 12, wherein:
the first filter is in a first input chamber at the input end, the first input chamber being in fluid communication with the first sensor chamber via a first flow pathway;
the second filter is in a second input chamber at the input end, the second input chamber being in fluid communication with the second sensor chamber via a second flow pathway; and
the first flow pathway is separate from the second flow pathway.

14. The plug of claim 12, wherein:
the first sensor is mounted on a first printed circuit board that is shaped to create a first flow pathway between the input end and the first sensor chamber; and
the second sensor is mounted on a second printed circuit board that is shaped to create a second flow pathway between the input end and the second sensor chamber.

15. The plug of claim 12, wherein:
the first sensor is mounted on a first printed circuit board that forms a boundary of the first sensor chamber; and
a first flow pathway between the input end and the first sensor chamber traverses an open space between an edge of the first printed circuit board and the housing.

16. The plug of claim 12, wherein the smoke taint compound is guaiacol or 4-methylguaiacol.

17. The plug of claim 12, wherein the second substance is acetic acid, sulfur dioxide, or hydrogen.

18. The plug of claim 12, wherein:
the first sensor comprises a plurality of sub-sensors;
individual sub-sensors of the plurality of sub-sensors detect different substances from each other; and
measurements from the individual sub-sensors are used to determine a presence of the smoke taint compound.

19. The plug of claim 12, wherein:
the first sensor comprises a plurality of sub-sensors;
individual sub-sensors of the plurality of sub-sensors operate at different biases from each other; and
measurements from the individual sub-sensors are used to determine a presence of the smoke taint compound.

20. The plug of claim 12, wherein:
the first sensor comprises a plurality of sub-sensors; and
measurements from individual sub-sensors of the plurality of sub-sensors determine a presence of phenols, to detect the smoke taint compound.

* * * * *